United States Patent
Jiang et al.

(10) Patent No.: US 11,535,543 B2
(45) Date of Patent: Dec. 27, 2022

(54) MEDIUM MATERIAL FOR REMOVING PHENOL CONTAMINATION FROM GROUNDWATER, METHOD OF PRODUCING THE SAME, AND USE OF THE SAME

(71) Applicant: CHINESE RESEARCH ACADEMY OF ENVIRONMENTAL SCIENCES, Beijing (CN)

(72) Inventors: Yonghai Jiang, Beijing (CN); Xinying Lian, Beijing (CN); Beidou Xi, Beijing (CN); Yu Yang, Beijing (CN); Yongfeng Jia, Beijing (CN); Fu Xia, Beijing (CN); Xu Han, Beijing (CN)

(73) Assignee: Chinese Research Academy of Environmental Sciences, Beijing (CN)

( * ) Notice: Subject to any disclaimer, the term of this patent is extended or adjusted under 35 U.S.C. 154(b) by 342 days.

(21) Appl. No.: 16/823,330

(22) Filed: Mar. 19, 2020

(65) Prior Publication Data
US 2020/0308035 A1    Oct. 1, 2020

(30) Foreign Application Priority Data

Mar. 28, 2019 (CN) .......................... 201910241315.8

(51) Int. Cl.
| | |
|---|---|
| *C02F 3/34* | (2006.01) |
| *C12N 5/00* | (2006.01) |
| *C12N 1/20* | (2006.01) |
| *C12N 11/00* | (2006.01) |
| *C02F 101/34* | (2006.01) |
| *C02F 103/06* | (2006.01) |

(52) U.S. Cl.
CPC ................ *C02F 3/34* (2013.01); *C12N 1/20* (2013.01); *C12N 5/0068* (2013.01); *C12N 11/00* (2013.01); *C02F 2101/345* (2013.01); *C02F 2103/06* (2013.01); *C12N 2500/14* (2013.01); *C12N 2500/20* (2013.01)

(58) Field of Classification Search
CPC ............ C12N 2500/20; C12N 2500/14; C12N 11/00; C12N 5/0068; C12N 1/20; C02F 2103/06; C02F 2101/345; C02F 3/34
See application file for complete search history.

(56) References Cited

FOREIGN PATENT DOCUMENTS

| CN | 101875928 | 11/2010 | |
|---|---|---|---|
| CN | 107653209 | 2/2018 | |
| CN | 108396024 | 8/2018 | |
| CN | 108996709 | 12/2018 | |
| CN | 108996709 A | * 12/2018 | ................ C02F 1/30 |

OTHER PUBLICATIONS

Kim, B. S., Lee, S. H., Park, Y. T., Ham, S. W., Chae, H. J., & Nam, I. S. (2001). Selective catalytic reduction of NOx, by propene over copper-exchanged pillared clays. Korean Journal of Chemical Engineering, 18(5), 704-710 (Year: 2001).*
Welz, P. J., Ramond, J. B., Cowan, D. A., & Burton, S. G. (2012). Phenolic removal processes in biological sand filters, sand columns and microcosms. Bioresource Technology, 119, 262-269 (Year: 2012).*
Yuen machine translation (Year: 2018).*
First Chinese Office Action, issued in the corresponding Chinese patent application No. 201910241315 8, dated Apr. 16, 2020, 21 pages (including translation).
Sun et al., "Adsorption performance and influencing factors of manganese sand filter media on phenol removal in drinking water treatment plant", Journal of Environmental Engineering Technology, vol. 8, No. 5, Sep. 2018, 9 pages.
"Advances in Mineral Processing Engineering Technology", Comprehensive Report, 2016-2017, 22 pages (including English Abstract) mentioned in Chinese Office Action.

* cited by examiner

*Primary Examiner* — Louise W Humphrey
*Assistant Examiner* — Trevor L Kane
(74) *Attorney, Agent, or Firm* — Hamre, Schumann, Mueller & Larson, P.C.

(57) ABSTRACT

A medium material for removing phenol contamination from groundwater, a method of producing the same, and use of the same id disclosed. In at least some embodiments, the medium material is a granular material which has an average particle diameter of 0.5-1.5 cm and is formed from a bacteria-entrapping solution, a manganese sand filter material, modified bentonite, and biochar at a mass ratio of 1:0.2-0.4:0.2-0.4:0.1-0.2 by a series of processes including strain culturing, catalysis, mixing, solidification, and the like. The medium material can remove phenol from groundwater, is a safe and environment-friendly material, has a long service life, and/or achieves waste treatment with waste.

11 Claims, No Drawings

MEDIUM MATERIAL FOR REMOVING PHENOL CONTAMINATION FROM GROUNDWATER, METHOD OF PRODUCING THE SAME, AND USE OF THE SAME

CROSS-REFERENCE TO RELATED APPLICATION

This application claims priority benefits from Chinese patent application No. 201910241315.8, filed on Mar. 28, 2019, which is hereby incorporated by reference herein in its entirety.

FIELD OF THE INVENTION

The present invention involves groundwater contamination remediation in the field of environmental protection, and in particular relates to a medium material for removing phenol contamination from groundwater, a method of producing the same, and use of the same.

Phenol is one of the phenolic compounds, with the simplest structure and the highest toxicity, and has biological toxicity. If entering the human body, phenol leads to teratogenic, carcinogenic, and mutagenic effects. Phenol is widely used in industries such as oil refining, coking, chemical industry, pharmaceutical industry, and the like. Environmental contamination of soil, surface water, and groundwater has been caused by wide use of chemical raw materials containing phenol as well as improper storage or unregulated emission of such chemical raw materials. Groundwater is an important water source for drinking and irrigation, and humans and crops are greatly harmed if groundwater is contaminated by phenol. Therefore, economical and efficient phenol remediation techniques for groundwater are important.

In various groundwater remediation techniques, the selection of medium materials directly affects the removal effects of contaminants and can be key for whether the remediation is effective or not. Current remediating materials for phenol in groundwater have several disadvantages including unremarkable remediation effects, short service life, and the like. An efficient and inexpensive medium material which can remove phenol from groundwater is desired.

SUMMARY OF THE INVENTION

A medium material for removing phenol contamination from groundwater, a method of producing the same, and use of the same to at least partly solve at least one of the technical problems described above is disclosed.

In some embodiments, a method of producing a medium material for removing phenol contamination from groundwater comprises:

(a) weighing an amount of organic bentonite and an amount of cupric nitrate at a mass ratio of 1:0.25, respectively, formulating a cupric nitrate solution, adding the organic bentonite to the cupric nitrate solution, withdrawing the organic bentonite and placing it into a heating equipment to increase the temperature to 250-300° C. at 10° C./min, and roasting for 30-45 min to obtain modified bentonite;

(b) culturing phenol-degrading bacteria extracted from a manganese sand filter material in a TSB medium with a concentration of 1±0.4% under ambient conditions of pH=6.0-7.3, 25° C., and a dissolved oxygen concentration of 8.15-8.40 mg/L for 10-24 h to form an active bacterial agent;

(c) adjusting an OD600 value of the active bacterial agent to near 1.0, inoculating to 100 mL of an MSVP medium containing 0.20-0.45 g/L of $SiO_2$ powder, and adding to 100 mL of a sodium alginate solution with a mass concentration of 0.5 g/L at a volume ratio of 10-20% after 15-24 h of adsorption to obtain a bacteria-entrapping solution; and (d) slowly adding the bacteria-entrapping solution, the manganese sand filter material, the modified bentonite, and biochar at a mass ratio of 1:0.2-0.4:0.2-0.4:0.1-0.2 to a $CaCl_2$ crosslinking solution to form agglomerates or spheres through crosslinking and coagulation, which are washed with sterile water to obtain immobilized granules or prills, which are the product of interest.

In at least some embodiments, the manganese sand filter material in step (b) is a waste manganese sand filter material produced in a manganese-removing filtration tank of a waterworks.

In at least some embodiments, the manganese sand filter material in step (d) is preliminarily freeze-dried and sieved to have an average particle diameter of 50±10 μm.

In at least some embodiments, the biochar in step (d) is straw biochar or bagasse biochar having an average particle diameter of 80±10 μm.

In at least some embodiments, the product of interest in step (d) has an average particle diameter of 0.5-1.5 cm.

A medium material for removing phenol contamination from groundwater is disclosed, wherein the medium material is granular and is formed by mixing and reacting a bacteria-entrapping solution, a manganese sand filter material, modified bentonite, and biochar at a certain ratio. In at least some embodiments the medium material has an average particle diameter of 0.5-1.5 cm. In at least some embodiments the bacteria-entrapping solution, the manganese sand filter material, the modified bentonite, and the biochar are calculated by mass ratio: bacteria-entrapping solution: manganese sand filter material: modified bentonite:biochar=1: 0.2-0.4:0.2-0.4:0.1-0.2.

In some preferred embodiments, the manganese sand filter material is a waste manganese sand filter material produced in a manganese-removing filtration tank of a waterworks.

In some preferred embodiments, the bacteria-entrapping solution is obtained by treating phenol-degrading bacteria extracted from the manganese sand filter material.

In some preferred embodiments, the modified bentonite is obtained by modifying organic bentonite with a cupric nitrate solution and has an average particle diameter of 0.2-0.5 mm.

In some preferred embodiments, the biochar has an average particle diameter of 0.5-1 mm.

In some preferred embodiments, the medium material for removing phenol from groundwater has a removal rate between 90% and 95% for phenol.

A medium material for removing phenol contamination from groundwater produced by the production method as described above is disclosed.

Use of a medium material for removing phenol contamination from groundwater produced by the production method as described above in a field of treating groundwater contamination is disclosed.

The medium material disclosed has at least one of following advantages:

In at least some embodiments, the medium material has relatively high adsorption characteristic and degradation characteristic for phenol, and has a removal rate of 95% or more for phenol;

In at least some embodiments, the medium material is safe and environmentally friendly and has a long service life, can be used as a remediating agent and/or a filler in the treatment of groundwater phenol contamination, and/or achieves waste treatment with waste.

DETAILED DESCRIPTION OF ILLUSTRATIVE EMBODIMENTS

A method of producing a medium material for removing phenol contamination from groundwater is disclosed. In some embodiments the method includes:

(a) weighing organic bentonite and cupric nitrate at a mass ratio of 1:0.1-0.25, respectively, formulating a cupric nitrate solution, adding the organic bentonite to the cupric nitrate solution, withdrawing the organic bentonite and placing it into a heating equipment to increase the temperature to 250-300° C. at 10° C./min, and roasting for 30-45 min to obtain modified bentonite;

(b) culturing phenol-degrading bacteria extracted from a manganese sand filter material in a TSB medium (Tryptone Soybean Broth medium) with a concentration of 1±0.4% under ambient conditions of pH=6.0-7.3, 25° C., and a dissolved oxygen concentration of 8.15-8.40 mg/L for 10-24 h to form an active bacterial agent;

(c) adjusting an OD600 value of the active bacterial agent to about 1.0, inoculating to 100 mL of an MSVP medium (an inorganic salt medium) containing 0.20-0.45 g/L of $SiO_2$ powder, and adding to 100 mL of a sodium alginate solution with a mass concentration of 0.5 g/L at a volume ratio of 10-20% after 15-24 h of adsorption to obtain a bacteria-entrapping solution; and (d) slowly adding the bacteria-entrapping solution, the manganese sand filter material, the modified bentonite, and biochar at a mass ratio of 1:0.2-0.4:0.2-0.4:0.1-0.2 to a $CaCl_2$ crosslinking solution to form agglomerates or spheres through crosslinking and coagulation, which are washed with sterile water to obtain immobilized granules or prills, which are the product of interest.

In at least some embodiments, the manganese sand filter material is freeze-dried and sieved to have an average particle diameter of about 50 μm.

In at least some embodiments, the biochar can be straw biochar or bagasse biochar having an average particle diameter of about 80 μm.

In at least some embodiments, the granular medium material finally obtained has an average particle diameter of 0.5-1.5 cm.

In some embodiments, a medium material for removing phenol contamination from groundwater is granular, i.e., the medium material is a granular material which has an average particle diameter of 0.5-1.5 cm and is formed from a bacteria-entrapping solution, a manganese sand filter material, modified bentonite, and biochar at a certain ratio by a series of processes including strain culturing, catalysis, mixing, solidification, and the like, wherein the bacteria-entrapping solution, the manganese sand filter material, the modified bentonite, and the biochar are calculated by mass ratio: bacteria-entrapping solution: manganese sand filter material: modified bentonite:biochar=1:0.2-0.4:0.2-0.4:0.1-0.2.

In at least some embodiments, the manganese sand filter material is a waste manganese sand filter material produced in a manganese-removing filtration tank of a waterworks.

In at least some embodiments, the bacteria-entrapping solution is obtained by treating phenol-degrading bacteria extracted from the manganese sand filter material.

In at least some embodiments, the modified bentonite is obtained by modifying organic bentonite with a cupric nitrate solution and has an average particle diameter of 0.2-0.5 mm.

In at least some embodiments, the biochar has an average particle diameter of 0.5-1 mm.

A large number of tests have shown that in, at least some embodiments, the medium material for removing phenol from groundwater has a removal rate between 90% and 95% for phenol.

Use of a medium material for removing phenol from groundwater in a field of treating groundwater contamination is also disclosed.

In some preferred embodiments, the method of producing a medium material for removing phenol from groundwater comprises:

a medium material that is granular, i.e., a granular material which has an average particle diameter of 0.5-1.5 cm and is formed from a bacteria-entrapping solution, a manganese sand filter material, modified bentonite, and biochar at a certain ratio by a series of processes including strain culturing, catalysis, mixing, solidification, and the like. In at least some embodiments, the manganese sand filter material is from a manganese-removing filtration tank of a waterworks, and is freeze-dried and sieved to have an average particle diameter of about 50 μm. In at least some embodiments, the bacteria-entrapping solution is obtained by culturing phenol-degrading bacteria extracted from a manganese sand filter material in a TSB medium with a concentration of 1% under ambient conditions of pH=6.0, 25° C., and a dissolved oxygen concentration of 8.15-8.40 mg/L for 12 h to form an active bacterial agent, and adjusting an OD600 value to about 1.0, inoculating to 100 mL of an MSVP medium containing 0.2 g/L of $SiO_2$ powder, and adding to 100 mL of a sodium alginate solution with a mass concentration of 0.5 g/L at a volume ratio of 10% after 24 h of adsorption. In at least some embodiments, the modified bentonite is formed by weighing organic bentonite and cupric nitrate at a mass ratio of 1:0.25, respectively, formulating a cupric nitrate solution, adding the organic bentonite to the cupric nitrate solution and stirring with magnetic suspension for 10 h followed by standing for 12 h, withdrawing the organic bentonite and placing it into a muffle furnace to increase the temperature to 300° C. at 10° C./min, roasting for 30 min, and naturally cooling. In at least some embodiments, the biochar has an average particle diameter of about 80 μm, and can be straw biochar or bagasse biochar. In at least some embodiments, a medium material has an average particle diameter of 0.5-1.5 cm is obtained by slowly adding the bacteria-entrapping solution, the manganese sand filter material, the modified bentonite, and the biochar described above at a mass ratio of 1:0.2-0.4:0.2-0.4:0.1-0.2 to a $CaCl_2$ crosslinking solution to form spheres through crosslinking and coagulation, which are washed with sterile water to obtain immobilized prills.

The following examples are meant for illustrative purposes but should not be viewed as limiting.

Example 1

A manganese sand filter material from a manganese-removing filtration tank of a waterworks was freeze-dried and sieved for stand-by. A bacteria-entrapping solution was obtained by culturing phenol-degrading bacteria extracted from the manganese sand filter material in a TSB medium with a concentration of 1.2% under ambient conditions of pH=6.5, 25° C., and a dissolved oxygen concentration of about 8.20 mg/L for 18 h to form an active bacterial agent, and adjusting an OD600 value to about 1.0, inoculating to 100 mL of an MSVP medium containing 0.3 g/L of $SiO_2$ powder, and adding to 100 mL of a sodium alginate solution with a mass concentration of 0.5 g/L at a volume ratio of 10% after 20 h of adsorption. Modified bentonite was obtained by weighing organic bentonite and cupric nitrate at a mass ratio of 1:0.25, respectively, formulating a cupric nitrate solution, adding the organic bentonite to the cupric nitrate solution and stirring with magnetic suspension for 10 h followed by standing for 12 h, withdrawing the organic bentonite and placing it into a muffle furnace to increase the temperature to 300° C. at 10° C./min, roasting for 30 min, and naturally cooling. Bagasse biochar was selected as the biochar, and had an average particle diameter of about 80 μm. A medium material having an average particle diameter of around 0.7 cm was finally obtained by slowly adding the bacteria-entrapping solution, the manganese sand filter material, the modified bentonite, and the biochar described above at a mass ratio of 1:0.2:0.25:0.1 to a $CaCl_2$ crosslinking solution to form spheres through crosslinking and coagulation, which are washed with sterile water to obtain immobilized prills.

50 kg of the medium material produced was used as a remediating agent for a permeable reactive barrier to remediate groundwater contaminated by phenol (a phenol concentration of 1 mg/L). In a 1-month period during which the permeable reactive barrier operated, it was found that the removal rate of the medium material for phenol was maintained to be 95.8% by detecting and analyzing the content of phenol.

Examples 2-4

The methods for producing medium materials for removing phenol from groundwater were the same as that of Example 1, except for the replacements of components or proportions as shown in Table 1 below.

Comparative Example 1

A medium material was formed according to one group of proportions and components eliminated by the solutions described above to test the removal rate of phenol.

TABLE 1

Components & Proportions of Examples 1-4 and Comparative Example 1.

| | | | Bacteria-entrapping solution | | Manganese sand filter material | Modified bentonite | Biochar | Phenol removal rate (%) |
|---|---|---|---|---|---|---|---|---|
| Example 1 | 1 | Organic bentonite:cupric nitrate | 1:0.25 | 0.2 | 0.25 | 0.1 bagasse biochar | 95.8 |
| | | Heating temperature | 300° C. | | | | |
| | | Heating time | 30 min | | | | |
| | | pH | 6.5 | | | | |
| | | Dissolved oxygen concentration | 8.20 mg/L | | | | |
| | | TSB medium concentration | 1.2% | | | | |
| | | culturing time | 18 h | | | | |
| | | $SiO_2$ concentration | 0.3 g/L | | | | |
| | | Adsorption time | 20 h | | | | |
| | | Volume proportion of sodium alginate solution | 10% | | | | |
| Example 2 | 1 | Organic bentonite:cupric nitrate | 1:0.15 | 0.25 | 0.3 | 0.15 straw biochar | 95.4 |
| | | Heating temperature | 350° C. | | | | |
| | | Heating time | 35 min | | | | |
| | | pH | 6 | | | | |
| | | Dissolved oxygen concentration | 8.20 mg/L | | | | |
| | | TSB medium concentration | 1% | | | | |
| | | culturing time | 12 h | | | | |
| | | $SiO_2$ concentration | 0.3 g/L | | | | |
| | | Adsorption time | 20 h | | | | |
| | | Volume proportion of sodium alginate solution | 20% | | | | |
| Example 3 | 1 | Organic bentonite:cupric nitrate | 1:0.25 | 0.25 | 0.4 | 0.1 straw biochar | 95.6 |
| | | Heating temperature | 260° C. | | | | |
| | | Heating time | 40 min | | | | |
| | | pH | 7 | | | | |
| | | Dissolved oxygen concentration | 8.25 mg/L | | | | |
| | | TSB medium concentration | 1.3% | | | | |
| | | culturing time | 24 h | | | | |
| | | $SiO_2$ concentration | 0.3 g/L | | | | |
| | | Adsorption time | 24 h | | | | |
| | | Volume proportion of sodium alginate solution | 10% | | | | |

TABLE 1-continued

Components & Proportions of Examples 1-4 and Comparative Example 1.

|  |  | Bacteria-entrapping solution |  | Manganese sand filter material | Modified bentonite | Biochar | Phenol removal rate (%) |
|---|---|---|---|---|---|---|---|
| Example 4 | 1 | Organic bentonite:cupric nitrate | 1:0.25 | 0.26 | 0.2 | 0.1 bagasse biochar | 95.9 |
|  |  | Heating temperature | 280° C. |  |  |  |  |
|  |  | Heating time | 45 min |  |  |  |  |
|  |  | pH | 6 |  |  |  |  |
|  |  | Dissolved oxygen concentration | 8.30 mg/L |  |  |  |  |
|  |  | TSB medium concentration | 0.8% |  |  |  |  |
|  |  | culturing time | 18 h |  |  |  |  |
|  |  | SiO$_2$ concentration | 0.44 g/L |  |  |  |  |
|  |  | Adsorption time | 20 h |  |  |  |  |
|  |  | Volume proportion of sodium alginate solution | 20% |  |  |  |  |
| Comparative Example 1 | 1 | Organic bentonite:cupric nitrate | 1:0.5 | 0.5 | 0.5 | 0.5 bagasse biochar | 78.2 |
|  |  | Heating temperature | 200° C. |  |  |  |  |
|  |  | Heating time | 20 min |  |  |  |  |
|  |  | pH | 5.5 |  |  |  |  |
|  |  | Dissolved oxygen concentration | 8 mg/L |  |  |  |  |
|  |  | TSB medium concentration | 1.5% |  |  |  |  |
|  |  | culturing time | 8 h |  |  |  |  |
|  |  | SiO$_2$ concentration | 0.5 g/L |  |  |  |  |
|  |  | Adsorption time | 10 h |  |  |  |  |
|  |  | Volume proportion of sodium alginate solution | 25% |  |  |  |  |

As can be seen, the effects of Examples 1-4 are far better than that of Comparative Example 1. The medium materials formed according to the proportions described above effectively removes phenol from groundwater.

The objects, technical solutions, and advantageous effects of the present invention are further illustrated in details by the specific example described above. It is to be understood that those described above are merely specific examples of the present invention, but are not intended to limit the present invention. All of modifications, equivalent replacements, improvements, and the like, which are within the spirit and the principle of the present invention, should be encompassed in the scope protected by the present invention.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A method of producing a medium material for removing phenol contamination from groundwater, comprising:
   (a) weighing an amount of organic bentonite and an amount of cupric nitrate at a mass ratio of 1:0.25, respectively, formulating a cupric nitrate solution, adding said amount of organic bentonite to said cupric nitrate solution, withdrawing said amount of organic bentonite and placing it into a heating equipment to increase the temperature to 250-300° C. at 10° C/min, and roasting for 30-45 min to obtain a modified bentonite;
   (b) culturing phenol-degrading bacteria extracted from a manganese sand filter material in a tryptic soy broth (TSB) medium with a concentration of 1±0.4% under ambient conditions of pH=6.0-7.3, 25° C., and a dissolved oxygen concentration of 8.15-8.40 mg/L for 10-24h to form an active bacterial agent;
   (c) adjusting an OD600 value of said active bacterial agent to near 1.0, inoculating to 100 mL of an MSVP medium containing 0.20-0.45 g/L of SiO2 powder, and adding to 100 mL of a sodium alginate solution with a mass concentration of 0.5 g/L at a volume ratio of 10-20% after 15-24 h of adsorption to obtain a bacteria-entrapping solution; and
   (d) adding said bacteria-entrapping solution, said manganese sand filter material, said modified bentonite, and an amount of biochar at a mass ratio of 1:(0.2-0.4):(0.2-0.4):(0.1-0.2) to a CaCl2 crosslinking solution to form agglomerates or spheres through crosslinking and coagulation, which are washed with sterile water to obtain immobilized granules or prills.

2. The method of claim 1, wherein said manganese sand filter material is a waste manganese sand filter material produced in a manganese-removing filtration tank of a waterworks.

3. The method of claim 1, wherein said manganese sand filter material is preliminarily freeze-dried and sieved to have an average particle diameter of 50±10 μm in step (d).

4. The method of claim 1, wherein said biochar is straw biochar or bagasse biochar having an average particle diameter of 80±10 μm.

5. The method of claim 1, wherein said immobilized granules or prills have an average particle diameter of 0.5-1.5 cm.

6. A granular medium material for removing phenol contamination from groundwater, formed by mixing a bacteria-entrapping solution, a manganese sand filter material, a modified bentonite, and a biochar at a mass ratio of 1:(0.2-0.4):(0.2-0.4):(0.1-0.2),
   wherein said medium material has an average particle diameter of 0.5-1.5 cm, wherein the modified bentonite is obtained by weighing an amount of organic bentonite and an amount of cupric nitrate at a mass ratio of 1:0.25, respectively, formulating a cupric nitrate solution, adding said amount of organic bentonite to said cupric nitrate solution, withdrawing said amount of organic bentonite and placing it into a heating equipment to increase the temperature to 250-300° C. at 10° C/min, and roasting for 30-45 min, and wherein the bacteria-entrapping solution is obtained by culturing phenol-degrading bacteria extracted from a manganese sand filter material in a tryptic soy broth (TSB) medium with a concentration of 1±0.4% under ambient conditions of pH=6.0-7.3, 25° C., and a dissolved oxygen concentration of 8.15-8.40 mg/L for 10-24h to form an active bacterial agent, adjusting an OD600 value of said active bacterial agent to near 1.0, inoculating to 100 mL of an MSVP medium containing 0.20-0.45 g/L of $SiO_2$ powder, and adding to 100 mL of a sodium alginate solution with a mass concentration of 0.5 g/L at a volume ratio of 10-20% after 15-24 h of adsorption.

7. The medium material for removing phenol contamination from groundwater according to claim 6, wherein said manganese sand filter material is a waste manganese sand filter material produced in a manganese-removing filtration tank of a waterworks;
said biochar has an average particle diameter of 0.5-1 mm.

8. The medium material for removing phenol contamination from groundwater according to claim 6, wherein said medium material has a removal rate between 90% and 95% for phenol.

9. A medium material for removing phenol contamination from groundwater produced by the method according to claim 1.

10. The medium material of claim 9, wherein said medium material has a removal rate between 90% and 95% for phenol.

11. The method of claim h further comprising using said medium material for removing phenol contamination from groundwater.

* * * * *